United States Patent [19]

Diago et al.

[11] Patent Number: 5,608,055
[45] Date of Patent: Mar. 4, 1997

[54] BETA LACTAM PRODUCTION

[75] Inventors: Jose Diago, Barcelona, Spain; Johannes Ludescher, Breitenbach, Austria

[73] Assignee: Biochemie Gesellschaft m.b.H., Austria

[21] Appl. No.: 471,943

[22] Filed: Jun. 6, 1995

Related U.S. Application Data

[63] Continuation of Ser. No. 368,935, Jan. 5, 1995, abandoned, which is a continuation of Ser. No. 914,244, Jul. 15, 1992, abandoned.

[30] Foreign Application Priority Data

Jul. 15, 1991 [GB] United Kingdom ............... 9115203

[51] Int. Cl.⁶ ............... C07D 501/18; C07D 501/57; C07D 498/02
[52] U.S. Cl. ............... 540/222; 540/230; 540/215; 540/301; 540/205
[58] Field of Search .................. 540/222, 225, 540/221, 215, 230, 301, 205

[56] References Cited

U.S. PATENT DOCUMENTS 4,073,902 2/1978 Scartazzini .................. 540/215
4,358,588 11/1982 Henniger .................. 424/246
4,358,988 11/1982 Henniger .................. 424/246

FOREIGN PATENT DOCUMENTS 54-059296 5/1979 Japan.
8403918 7/1984 Spain.
WO91/17166 11/1991 WIPO.

OTHER PUBLICATIONS

J. Med. Chem., vol. 9, 746 (1966) Spencer, et al.
C.A.91(1):5236v, Juste Sese(1979).
CA 85 (23):177405s, Hebron, S. A. (1976).
CA 86 (9):55467p. Juste (1977).
CA 89 (13):109467w, Cuixart Grande (1978).
CA 106:119004b, Cabri, et al. (1987).

Primary Examiner—John M. Ford
Assistant Examiner—Pavanaram K. Sripada
Attorney, Agent, or Firm—Robert S. Honor; Melvyn M. Kassenoff; Thomas O. McGovern

[57] ABSTRACT

A new process is described for the production of 7-alpha-aminoacyl-cephalosporin free from halogen-containing solvents by acylating 7-amino-ceph-3-em-4-carboxylic acid or a derivative thereof in a halogen-free solvent.

17 Claims, No Drawings

BETA LACTAM PRODUCTION

This is a continuation of application Ser. No. 08/368,935, filed Jan. 5, 1995, now abandoned, which in turn is a continuation of application Ser. No. 07/914,244, filed Jul. 15, 1992, now abandoned.

This invention relates to a process for the production of a highly pure 7-alpha-aminoacyl-cephalosporins other than 7-alpha-aminoacyl-desacetoxycephalosporins, hereinafter referred to as compounds of the invention which on the industrial scale is economical to operate, and is environmentally acceptable, avoiding the use of halogen-containing solvents such as methylene chloride.

Many processes have been investigated for the industrial production of the compounds of the invention. Such processes must meet the necessary criteria for adoption on a commercial scale e.g. high yield, economy and ease of operation, including easy and effective purification of the end product, and few reaction steps. Processes which have been operated commercially on a large scale have required the use of halogen-containing solvents such as methylene chloride, despite the fact that these solvents are difficult to recycle or dispose of in an environmentally acceptable manner. The compounds of the invention produced also inevitably contain trace amounts of solvents and in the case of halogen-containing solvents such as methylene chloride, this is undesirable since there are fears that these could be carcinogenic.

In the literature there is no general or clear teaching of how varying reaction conditions, reactants, solvents or other factors in the synthesis of the compounds of the invention and their solvates affect yields, purity etc. This my be due to the fact that the cephalosporin nucleus is very labile, several reactive moieties are present. The art is thus very empirical.

In U.S. Pat. No. 4,07,3902 cefroxadine is prepared in methylene chloride by reacting a mixed anhydride of an amino protected α-amino-α-(1,4-cyclohexadienyl)acetic acid with 7-amino-3-methoxy-3-cephem-4-carboxylic acid diphenylmethyl ester and subsequent removal of the protecting groups.

In U.S. Pat. No. 3,422,103 cephaloglycin is prepared by reacting a mixed anhydride of a lower alkanoic acid and a N-trityl amino acid with 7-aminocephalosporanic acid in chloroform (yield 29,5%) and thereafter removing the trityl group by hydrolysis with acetic acid (yield 37,8%) or by hydrogenolysis with palladium on carbon (yield 7,1%).

U.S. Pat. No. 3,925,372 describes the synthesis of cefaclor in toxic acetonitrile. The cephem nucleus is first sylated and reacted then with a mixed anhydride formed from chloroformic acid ester and a Dane salt. The yield is low, 44%.

Methylene chloride is a widely used solvent because of its physical properties e.g. low boiling point, thus easy removal. Despite these advantages the use of methylene chloride and other halogen containing solvents have been criticised for years. Environmental problems arise in its use since methylene chloride is not biologically degradable. Emission controls on manufacturing plants using chlorinated hydrocarbons are contemplated. Various Pharmacopeia Commissions are considering the possibility of reducing methylene chloride residues in pharmaceuticals. The problem is especially acute for antibiotics since the proposed limits of 100–500 ppm residual methylene chloride is far exceeded in the case of antibiotics (usual values 1000 to 3000 ppm).

There was thus a clear need to find alternative industrially viable syntheses of the compounds of the invention. After exhaustive testing we have found a new synthesis for the production of these compounds which possesses a number of significant practical and economic advantages in industrial use. We have surprisingly found that it is suitable for a very wide variety of cephems with a wide variety of 3-substituents. It uses only solvents which do not contain halogen atoms and are environmentally acceptable, gives high yields of at least 80 to 85 percent or, in some cases, even over 90 percent and produces highly pure products. It also obviates the need for equipment for generating vacuum, sealing and safety problems, which result from the use of e.g. acetonitrile or acetone as solvent. Furthermore it is economical in operation and yet complicated purification techniques are avoided. The process is applicable to the synthesis of a wide variety of 7-alpha-aminoacyl-cephalosporins.

Accordingly in another aspect the invention provides a process for the production of a compound of the invention without the use of a halogen-containing solvent which comprises the steps of (i) producing a mixed carboxylic acid anhydride by reacting an N-substituted vinyl alpha-amino acid with an appropriate acylating agent in a solvent which does not contain halogen atoms and which is water-immiscible or sparingly soluble in water, and (ii) further reacting the resultant mixed carboxylic acid anhydride with a 7-amino-ceph-3-em-4-carboxylic acid or a derivative thereof in a solvent which does not contain halogen atoms.

In particular the present invention provides a process for the production of a cephem of formula I

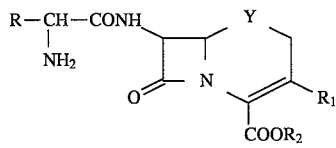

wherein
R is phenyl, 4-hydroxyphenyl or 1,4-cyclohexadien-1-yl
Y is oxygen, sulphur or methylene,
$R_1$ is hydrogen, halogen, alkoxy, ethyl, a group of formula

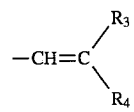

wherein
$R_3$ and $R_4$, which may be the same or different, are hydrogen, or a $(C_{1-6})$ aliphatic, $(C_{3-7})$cycloaliphatic, $(C_{7-10})$araliphatic, $(C_{6-12})$aromatic, cyano or lower alkoxycarbonyl;
or a group of formula —$CH_2Z$,
wherein Z has one of the following meanings
a) a group of formula

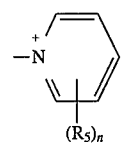

wherein
n is 0 or an integer from 1 to 5 and each $R_5$, which when n is from 2 to 5, may be the same or different, is an aliphatic, an aryl, an araliphatic, alkoxymethyl, formyl, acyloxy, acyloxymethyl, esterified carboxyl;

alkoxy, aryloxy, aralkoxy, alkylthio, arylthio; aralkylthio; cyano, hydroxy, carbamoyl, N-monoloweralkylcarbamoyl, N,N-diloweralkylcarbamoyl, N-(hydroxyloweralkyl)carbamoyl or carbamoylloweralkyl group;

b) azido;

c) amino or acylamido;

d) a derivative of a residue of a nucleophile obtained by reacting a compound, wherein Z is azido with a acetylenic, ethylenic or cyano dipolarophile (e.g. as disclosed in U.S. Pat. No. 4,024,133, the contents of which are incorporated herein by reference), e) a group of formula

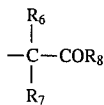

wherein $R_6$ and $R_7$, which may be the same or different, are selected from hydrogen, cyano, lower alkyl, phenyl, substituted phenyl, lower alkoxycarbonyl, mono- or diaryl lower alkoxycarbonyl, lower alkylcarbonyl, aryl lower alkyl and $C_5$ or $C_6$ cycloalkyl and $R_8$ is hydrogen, lower alkyl, phenyl, substituted phenyl, aryl lower alkyl and $C_5$ or $C_6$ cycloalkyl;

f) a group of formula

wherein $R_9$ is an aliphatic, araliphatic alicyclic, aromatic or heterocyclic group, and m is 0, 1 or 2;

g) a group of formula

wherein $R_{10}$ is hydrogen, lower alkyl, lower alkenyl, lower alkynyl, lower cycloalkyl, lower cycloalkyl lower alkyl, aryl, aryl lower alkyl, a heterocyclic group or a heterocyclyl lower alkyl, which may be optionally substituted by one or more lower alkoxy, lower alkylthio, halogen, lower alkyl, nitro, hydroxy, acyloxy, carboxy, carbalkoxy, lower alkylcarbonyl, lower alkylsulfonyl, lower alkoxysulfonyl, amino lower alkyl amino or acylamido groups, h) acetoxy;

i) a group —$OCOR_{11}$, wherein $R_{11}$ is
  ia) a straight or branched chain alkyl group of 2 to 7 carbon atoms, which may be interrupted by oxygen, sulfur or imino, and substituted by cyano, carboxyl, alkoxycarbonyl, hydroxy, carboxycarbonyl, halogen or amino;
  ib) a straight or branched chain alkenyl group of 2 to 7 carbon atoms, which may be interrupted by oxygen, sulfur or imino;
  ic) optionally substituted aryl or heterocyclyl or cycloalkyl;
  id) arylalkyl, heterocyclyl-alkyl or cycloalkylalkyl, which may be substituted in the ring;

j) a group of formula

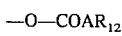

wherein

A is oxygen, sulfur or imino and $R_{12}$ is hydrogen, methyl or $R_{11}$;

k) a group of formula

wherein Q is fluorine, chlorine, bromine or iodine and E is an integer of 1 to 4, and $R_2$ represents hydrogen, a cation, a carboxy-protecting group or $COOR_2$ is $COO^-$, when $R_1$ is a positive charged group, without the use of halogen-containing solvent which comprises the steps of (i) producing a mixed carboxylic acid anhydride by reacting a N-substituted vinyl alpha-amino acid with an appropriate acylating agent in a solvent which does not contain halogen atoms and which is water-immiscible or sparingly soluble in water, and (ii) further reacting the resultant mixed carboxylic acid anhydride with a compound of formula II

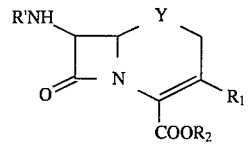

wherein Y, $R_1$ and $R_2$ are as defined above and R' is hydrogen or an amino protecting group in a solvent which does not contain halogen atoms.

Preferred values for $R_1$ are hydrogen, halogen, alkoxy, a group of formula

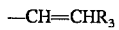

wherein $R_3$ is hydrogen, $(C_{1-6})$alkyl or a $(C_{6-12})$aromatic group or $R_1$ is a group of formula

wherein Z is a group of formula

in which $R_9$ is a heterocyclic group or Z is acetoxy.

In the definition of $R_9$, the term "heterocycle" includes single or fused rings comprising up to four hetero atoms in the ring selected from oxygen, nitrogen and sulphur and optionally substituted up to three $(C_{1-4})$alkyl, $(C_{1-4})$alkoxy, halogen, trihalo-$(C_{1-4})$alkyl, hydroxy, oxo, mercapto, amino, carboxyl, carbamoyl, di-$(C_{1-4})$alkyl-amino, carboxymethyl, carbamoylmethyl, sulfomethyl and methoxycarbonylamino.

Examples of heterocycle include unsubstituted and substituted imidazolyl, diazolyl, triazolyl, tetrazolyl, thiazolyl, thiadiazolyl, thiatriazolyl, oxazolyl, oxadiazolyl, benzimidazolyl, benzoxazolyl, benzothiazolyl, triazolylpyridyl, purinyl, pyridyl, pyrimidinyl, pyridazinyl, pyrazolyl and triazinyl.

Suitable heterocycles include unsubstituted and substituted 1,2,3-triazolyl; 1,2,4-triazolyl; tetrazolyl; oxazolyl; thiazolyl; 1,3,4-oxadiazolyl; 1,3,4-thiadiazolyl or 1,2,4-thiadiazolyl. Preferably the heterocycle is 1-methyl-1H-tetrazol-5-yl, 2-methyl-1,3,4-thiadiazol-5-yl, 1-carboxymethyl-1H-tetrazol-5-yl, 6-hydroxy-2-methyl-5-oxo-2H-1,2,4-triazin-3-yl and 1,2,3-triazol-5-yl.

Particularly preferred values for $R_9$ are 1-methyl-1H-tetrazol-5-yl and 1,2,3-triazol-5-yl.

As used herein "aryl" or "aromatic" is preferably phenyl, and alkyl preferably is $(C_{1-4})$ alkyl.

In the definition of $R_2$ a cation includes an alkali metal, an alkaline earth metal, ammonium or substituted ammonium. The term "carboxy protecting group" includes conventional silyl protecting groups, e.g. trialkylsilyl.

The process of the invention is useful for the preparation of a wide variety of 7-alpha-aminoacyl-cephalosporins, e.g. cefaclor, cephaloglycin, cefatrizine, cefroxadine, cefprozil or loracarbef.

Examples of a N-substituted vinyl alpha-amino acid are alpha-amino acids, wherein the amino group bears a protecting group as e.g. 1-methoxycarbonyl-propen-2-yl, 1-ethoxycarbonyl-propen-2-yl, 1-acetyl-propen-2-yl, 1-benzoyl-propen-2-yl, 1-(4-methoxy-benzoyl)-propen-2-yl or 1-(2,6-dimethoxy-benzoyl)-propen-2-yl.

The N-substituted vinyl alpha-amino acid can be employed as its salt. Examples of a salt are potassium, sodium, dicyclohexylammonium, N-methylpiperidinium or N-methylmorpholinium salts. Preferably salts are employed, more preferably Dane salts.

Examples of Dane salts suitable for the production of cefaclor, cephaloglycine, cefatrizine or cefroxadine include sodium or potassium D-N-(1-methoxycarbonylpropen-2-yl)-α-aminophenylacetate, sodium or potassium D-N-(1-ethoxycarbonyl-propen-2-yl)-α-aminophenylacetate, sodium or potassium D-N-(1-methoxycarbonylpropen-2-yl)-α-amino-p-hydroxyphenylacetate, or sodium or potassium D-N-(1-ethoxycarbonyl- propen-2-yl)-α-amino-p-hydroxyphenylacetate, sodium or potassium D-N-(1-methoxycarbonylpropen-2-yl)-α-amino-2-(1,4-cyclohexadien-1-yl)-acetate.

The acylating agent is for example a reactive acid derivative of a $C_4$–$C_9$ acid. Suitable reactive derivatives include acid halides, e.g. an acid chloride. The acid may be an aliphatic, alicyclic, or aromatic acid. The acid may be for example an alkanoic acid such as pivalic acid or 2-ethylhexanoic acid. If desired the acid may contain an aromatic ring, e.g. benzoic acid. Preferred acylating agents are pivaloyl chloride, 2-ethyl-hexanoyl chloride and benzoyl chloride. Alternatively the acylating agent may be a chloroformic acid alkyl ester, e.g. ethyl chloroformate.

The formula of the mixed anhydride is preferably as follows:

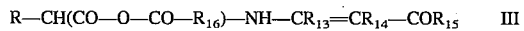

wherein

R is as defined above, $R_{13}$ is a $(C_{1-3})$alkyl group, preferably methyl, $R_{14}$ is hydrogen or $(C_{1-3})$alkyl group, preferably hydrogen, $R_{15}$ is a $(C_{1-4})$alkyl group, preferably methyl or ethyl; a $(C_{1-4})$alkoxy group, preferably methoxy or ethoxy; phenyl optionally substituted by alkoxy, $R_{16}$ is an aliphatic, alicyclic, or aromatic group, e.g. a $(C_{3-8})$alkyl group, or preferably phenyl or 1-ethylpentyl, or especially tert-butyl, and preferably wherein the amino group and the carbonyl group attached to the double bond have the cis configuration.

A small amount of a free $C_4$–$C_9$ acid may also be present in the production of the mixed anhydride. The acid is for example a $C_4$–$C_9$ acid. The acid may be for example an alkanoic acid such as pivalic acid or 2-ethylhexanoic acid. If desired the acid may contain an aromatic ring, e.g. benzoic acid.

The side chain of the free acid may be the same or different to that of the acylating agent. The preferred free acid is 2-ethylhexanoic acid or pivalic acid.

As indicated above in step i) there are used solvents which do not contain any halogen atoms. The term "sparingly soluble" includes solvents which are insoluble or slightly soluble in water. Examples of such solvents which are water-immiscible or sparingly soluble in water include those of low dielectric constant, e.g. appropriate ketones, esters and aromatic hydrocarbons. Examples include methyl-$(C_{2-4})$alkyl-ketones, such as methyl isobutyl ketone (hereinafter MIBK), di-$(C_{2-4})$alkyl-ketones, $(C_{1-3})$alkanoic acid butyl esters such as n-butyl acetate (hereinafter NBA), $(C_{1-3})$alkanoic acid propyl esters such as isopropylacetate and toluene. Preferred solvents include MIBK, NBA and isopropylacetate.

Naturally the solvent system used in step i) may contain more than one solvent, provided that halogen-containing solvents are not used.

The solvent used in the formation of the mixed anhydride step may comprise one or more solvents, provided that the system as a whole is water-immiscible or sparingly soluble in water.

Thus if desired a small amount of a co-solvent may be present in step i) which improves or activates the reaction of a Dane salt with the acid halide or other acylating agent.

We prefer to use as a co-solvent an organic amide such as a formamide or an acetamide, or their N-mono or N,N-dimethyl derivatives, e.g. dimethyl formamide, or preferably N-methylacetamide, N,N-dimethylacetamide, or N-methylpyrrolidine or tetramethylurea. Also a branched chain alcohol such as isopropanol is suitable.

Preferably a base, e.g. a tertiary amine base, is present as a catalyst for mixed carboxylic acid anhydride formation. Preferred catalysts include pyridines, for example a picoline, e.g. 3- or 4-picoline, or a lutidine.

The formation of the mixed carboxylic acid anhydride may be effected, e.g. at temperatures, from –50° to 50° C., and preferably from –40° to 0° C.

The product of step i) is generally a solution or a suspension of the mixed carboxylic acid anhydride which can be used further as such. If desired this anhydride may be maintained between step i) and step ii) at from ca. –60° to –20° C.

The step ii) is an acylation reaction of a 7-amino-ceph-3-em-4-carboxylic acid, in particular of a compound of formula II which is preferably in salt form.

Conveniently a solution of the salt of a 7-amino-ceph-3-em-4-carboxylic acid, in particular of a compound of formula II is added to the reaction mixture resulting from the mixed carboxylic acid anhydride formation. Alternatively a N-silylated 7-amino-ceph-3-em-4-carboxylic acid, in particular a N-silylated compound of formula II may be employed (R' is a silyl protecting group e.g. trialkyl$(C_{1-4})$silyl).

Thus the solvents indicated above as preferably used for the mixed carboxylic acid anhydride formation are also conveniently present in the acylation step.

The salt of a 7-amino-ceph-3-em-4-carboxylic acid, in particular of a compound of formula II is preferably in a solution or suspension in an organic solvent miscible with the solvent system used in the mixed carboxylic acid anhydride step and not containing halogen atoms.

The solvent system used for dissolving or suspending the salt of a compound of formula II is preferably an alkanol, e.g. $(C_1$–$C_4)$alkanol, e.g. ethanol, and preferably a $(C_{3-4})$alkanol, e.g. butanol or especially isopropanol, optionally in combination with a solvent used in step i).

If desired a small amount of water may be present.

If desired small amounts of a $(C_{4-9})$alkanoic acid e.g. 2-ethylhexanoic acid may be added to the mixture of the salt of a 7-amino-ceph-3-em-4-carboxylic acid, in particular of a compound of formula II, and solvent.

Preferred salts include secondary or tertiary amine salts e.g. 1,8-diazabicyclo[5,4,0]undec-7-ene or tetramethylguanidine.

Suitable reaction temperatures for the acylation step may be from about −60° C. to room temperature, preferably at or under −15° C.

The reaction mixture of the acylation step may be worked up in conventional manner. The protected 7-alpha-aminoacyl-cephem may be deprotected using known methods. The substituted vinyl group may be split by hydrolysis in aqueous acid.

The final product may be isolated in conventional manner, by adjusting pH. Purity may be very high, e.g. above 98%. The isolated product may contain traces of solvent residues, but is free from halogen-containing solvent.

In a preferred embodiment the invention provides a process for the production of a compound of the invention without the use of a halogen-containing solvent which comprises the steps of i) producing a mixed acid anhydride by reacting a N-substituted vinyl alpha-amino acid with an appropriate acylating agent in a solvent which does not contain halogen atoms and which is water-immiscible or sparingly soluble in water, and (ii) further reacting the resultant mixed acid anhydride with a salt of a 7-amino-ceph-3-em-4-carboxylic acid or derivative thereof in a solvent which does not contain halogen atoms.

Insofar as the production of any starting material used in the process of the invention, e.g. the Dane salt, is not particularly described herein this is known or may be made in analogous manner to known processes.

The following non-limitative examples illustrate the invention. All temperatures are in degrees Centigrade and are uncorrected.

In the examples the following abbreviations are used:
NBA=n-butyl acetate
IPA=isopropanol
Dane salt A=Potassium D-N-(1-ethoxycarbonylpropen-2-yl) α-aminophenylacetate
Dane salt B=Potassium D-N-(1-ethoxycarbonylpropen-2-yl) α-amino-p-hydroxyphenylacetate
DBU=1,8-diazabicyclo[5,4,0]undec-7-ene
TMG=tetramethylguanidine
TEA=triethylamine
7-ACA=7-aminocephalosporanic acid
7-ACCA=3-chloro-7-amino-3-cephem-4-carboxylic acid
TET-ACA=3-[(1-methyl-1H-tetrazol-5-yl)thiomethyl]-7-amino 3-cephem-4-carboxylic acid The yield given is based on the 7-amino-ceph-3-em-4-carboxylic acid derivative used as starting material. Purity is measured by HPLC on anhydrous basis.

The examples illustrate in step i) the mixed carboxylic acid anhydride formation, in step ii) the acylation of the beta-lactam using the mixture obtained in step i) without isolation, and in step iii) working up, including deprotection, to give the product.

EXAMPLE 1

3-[(Acetyloxy)methyl]-7-[(aminophenylacetyl)amino]-8-oxo-5-thia-1-azabicyclo[4.2.0]oct-2-ene-2-carboxylic acid (Cephaloglycin)

i) $4.6 \times 10^{-3}$ ml 4-picoline are added to a suspension of 10.014 g Dane salt A in 46 ml NBA. The resultant mixture is stirred for 5 minutes at room temperature and cooled to −15° C.; 3.8 ml benzoylchloride are added. The resultant suspension is stirred at −10° C. for 60 minutes, 15 ml NBA are added and then cooled to −55° C. giving a mixture containing the mixed carboxylic acid anhydride.

ii) 7.62 g 7-ACA are added to a mixture of 12 ml IPA and 12 ml NBA. The resulting suspension is cooled to 10° C and 3.69 ml TMG are added. The mixture is stirred for 15 minutes to give a yellow solution. This solution is added dropwise to the mixture obtained in step i) at a temperature of −55° C. to −50° C. over 20 minutes and the reaction mixture is stirred for a further 15 minutes at the same temperature and then for 3 hours at a temperature of −30° to −40° C. HPLC gives a cephaloglycin yield of 93%.

iii) The resultant crude protected cephaloglycin mixture is worked up by treating with a mixture of 27 ml ice-water and 6 ml concentrated HCl and stirred for 15 minutes while cooling with ice. The aqueous phase is separted off and the organic phase is back-extracted with 2 ml ice-water. The combined aqueous phases are heated to 25° C. and TEA is added until a pH value of 4.5/4.7 is reached. The title compound is obtained in the dihydrate form by standing the mixture 30 minutes, filtering the crystals and washing then with 30 ml ice-water and 30 ml 80% acetone, followed by drying. Yield 84.2%.

EXAMPLE 2

7-[(aminophenylacetyl)amino]-3-[[(1-methyl-1h-tetrazol)-5-yl) thio]methyl]-8-oxo-5-thia-1-azabicyclo [4.2.0]oct-2-ene-2-carboxylic acid i) $4.6 \times 10^{-3}$ ml 4-picoline are added to a suspension of 10.014 g Dane salt A in 25 ml NBA and 28 ml dimethylformamide. The resultant mixture is stirred for 5 minutes at room temperature and cooled to −15° C., 3.8 ml benzoylchloride are added. The solid is dissolved giving a fluid solution which is stirred at −10° C. for 60 minutes and then cooled to −55° C. giving a mixture containing the mixed carboxylic acid anhydride.

ii) 9.194 g of TET-ACA are added to a mixture of 10 ml IPA and 5 ml dimethylformamide. The resulting suspension is cooled to 10° C. and 3.69 ml TMG are added. The mixture is stirred for 15 minutes to give a pale brownish solution. This solution is added dropwise to the mixture obtained in step i) at a temperature of −55° C. to −50° C. over 30 minutes and the reaction mixture is stirred for 1 hour at a temperature of −50° to −40° C. and for 2 hours at a temperature of −40° C. to −30° C. HPLC shows the formation of the title compound with a yield of 94%.

iii) The mixture of step ii) is worked up by adding a mixture of 27 ml ice-water and 5 ml concentrated HCl and stirred for 15 minutes while cooling with ice. The phases are divided and the acidic aqueous phase is diluted with 50 ml water and treated slowly with triethylamine to bring the pH to 4.5.

The title compound separates out, is collected by filtering and washing followed by drying as in Example 1.

EXAMPLE 3

7-[[amino(4-hydroxyphenyl)acetyl]amino]-3-[[(1-methyl-1H-tetrazol)-5-yl) thio]methyl]-8-oxo-5-thia-1-azabicyclo-[4.2.0]oct-2-ene-2-carboxylic acid (PRECEFOPERAZONE)

i) 0.096 ml 4-picoline are added to a suspension of 10.47 g Dane Salt B in 25 ml NBA and 28 ml dimethylacetamide. The resultant mixture is stirred for 5 minutes at room temperature and cooled to −15° C.; 3.77 ml benzoylchloride are added. The resultant suspension is stirred at −10° C. for 60 minutes and then cooled to −55° C. giving a mixture containing the mixed carboxylic acid anhydride.

ii) 9.194 g of TET-ACA are added to a mixture of 7.5 ml IPA and 7.5 ml dimethylacetamide. The resulting suspension is cooled to 10° C. and 3.69 ml TMG are added. The mixture is stirred for 15 minutes to give a pale brownish solution. This solution is added dropwise to the mixture obtained in step i) at a temperature of −55° C. to −50° C. over 30 minutes and the raction mixture is stirred for 1 hour at a temperature of −50° to −40° C. and for 2 hours at a temperature of −40° C. to −30° C. HPLC shows the formation of the title compound with a yield of 87%.

iii) The mixture is worked up in analogous manner to Example 3.

EXAMPLE 4

7-[(aminophenylacetyl)amino]-3-[chloro]-8-oxo-5-thia-1-azabicyclo [4.2.0]oct-2-ene-2-carboxylic acid (CEFACLOR)

$2.3 \times 10^{-3}$ ml 4-picoline are added to a suspension of 5.02 g Dane Salt A in 23 ml NBA. The resultant mixture is stirred for 5 minutes at room temperature and cooled to −15° C., 1.93 ml benzoyl chloride are added. The resultant suspension is stirred at −10° C. for 60 minutes and then cooled to −55° C. giving a mixture containing the mixed carboxylic acid anhydride.

ii) 3.287 g 7-ACCA are added to a mixture of 5.5 ml IPA and 5.5 ml NBA. The resulting suspension is cooled to 10° C. and 2.2 ml DBU are added. The resulting mixture is stirred for 15 minutes to give a pale brownish solution, which is added dropwise to the mixture obtained in step i) at a temperature of −55° C. to −50° C. over 30 minutes. The reaction mixture is stirred at a temperature of −55° C. to −50° C. for 15 minutes and then for 1 hour at a temperature of −30° C. to −40° C. HPLC gives a Cefaclor yield of 87%.

iii) The resultant crude protected Cefaclor mixture is worked up by treating with a mixture of 13.5 ml ice-water and 2.0 ml concentrated HCl and stirred for 25 minutes while cooling with ice. The aqueous phase is separated off and the organic phase is back-extracted with 1.25 ml ice-water. The combined aqueous phases are mixed with 30 ml dimethylformamide, and the resulting suspension is cooled to 15° C., filtered and the solid washed with 8 ml dimethylformamide, which are added to the filtrate. The final solution is treated slowly with concentrated aqueous ammonia to bring the pH to 6.8. The cristalline suspension is stirred at 20° C. for 1 hour, filtered and the crystals washed with 16 ml acetone. After drying, 5.86 g of the title compound were obtained as dimethylformamide solvate.

EXAMPLE 5

Cefaclor i) $2.3 \times 10^{-3}$ ml 4-picoline are added to a suspension of 5.02 g Dane Salt A in 23 ml isopropylacetate. The resultant mixture is stirred for 5 minutes at room temperature and cooled to −15° C., 1.93 ml benzoylchloride are added. The resultant suspension is stirred at −10° C. for 60 minutes and then cooled to −55° C. giving a mixture containing the mixed carboxylic acid anhydride.

ii) 3.287 g 7-ACCA are added to 11 ml IPA. To the resulting suspension 1.84 ml TMG are added. After stirring for 15 minutes, a pale brownish solution is obtained. This solution is added dropwise to the mixture obtained in step i) at a temperature of −55° C. to −50° C. over 30 minutes. The reaction mixture is stirred at a temperature of −55° C. to −50° C. over 30 minutes. The reaction mixture is stirred at a temperature of −55° C. to −50° C. for 15 minutes and then for 1 hour at a temperature of −30° C. to −40° C. HPLC analysis of the mixture gives a Cefaclor yield of 84%.

iii) the mixture is worked up in analogous manner to Example 4 step iii)

Example 5 is repeated with the following changes:

a) the same quantity of isobutylacetate is used instead of isopropyl acetate in step i). HPLC yield in Cefaclor: 84%.

What is claim is:

1. In a process for the production of a 7-alpha-aminoacyl-cephem other than a 7-alpha-aminoacyl-desacetoxy-cephalosporin which comprises the steps of:

i) producing a mixed carboxylic acid anhydride by reacting an N-substituted vinyl alpha-amino acid with an acylating agent; and ii) reacting the mixed carboxylic acid anhydride with a 7-amino-ceph-3-em-4-carboxylic acid or derivative thereof, the improvement which comprises carrying out step i) in a solvent which does not contain a halogen atom and which is water-immiscible or sparingly soluble in water and is selected from ketones, esters, aromatic hydrocarbons, and mixtures thereof;

and carrying out step ii) with a non-silylated 7-amino-ceph-3-em-4-carboxylic acid or derivative thereof in a solvent which does not contain a halogen atom and is selected from ketones, esters, aromatic hydrocarbons, alkanols, and mixtures thereof.

2. A process according to claim 1 for the production of a compound of formula I,

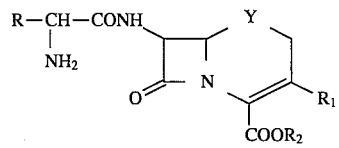

wherein

R is phenyl, 4-hydroxyphenyl or 1,4-cyclohexadien-1-yl,

Y is oxygen, sulphur or methylene, $R_1$ is hydrogen, halogen, alkoxy, ethyl, a group of formula

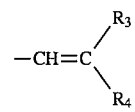

wherein $R_3$ and $R_4$, which may be the same or different, are hydrogen or, a $(C_{1-6})$aliphatic, $(C_{3-7})$cycloaliphatic, $(C_{7-10})$araliphatic, $(C_{6-12})$aromatic, cyano or lower alkoxycarbonyl group;

or a group of formula —$CH_2Z$, wherein Z has one of the following meanings a) a group of formula

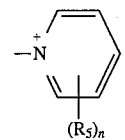

wherein n is 0 or an integer from 1 to 5 and each $R_5$, which when n is from 2 to 5 may be the same or different, is an aliphatic, an aryl, an araliphatic, alkoxymethyl, formyl acyloxy, acyloxymethyl, esterified carboxyl, alkoxy, aryloxy, aralkoxy, alkylthio, arylthio, aralkylthio; cyano, hydroxy, carbamoyl, N-monoloweralkylcarbamoyl, N,N-diloweralkylcarbamoyl, N-(hydroxyloweralkyl)carbamoyl or carbamoylloweralkyl group;

b) azido, c) amino or acylamido;

d) a derivative of a residue of a nucleophile obtained by reacting a compound, wherein Z is azido with a acetylenic, ethylenic or cyano dipolarophile, e) a group of formula

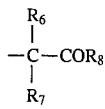

wherein $R_6$ and $R_7$, which may be the same or different, are selected from hydrogen, cyano, lower alkyl, phenyl, substituted phenyl, lower alkoxycarbonyl, mono- or diaryl lower alkoxycarbonyl, lower alkylcarbonyl, aryl lower alkyl and $C_5$ or $C_6$ cycloalkyl and $R_8$ is hydrogen, lower alkyl, phenyl, substituted phenyl, aryl lower alkyl and $C_5$ or $C_6$ cycloalkyl;

f) a group of formula

wherein $R_9$ is an aliphatic, araliphatic, alicyclic, aromatic or heterocyclic group, and m is 0, 1 or 2;

g) a group of formula

wherein $R_{10}$ is hydrogen, lower alkyl, lower alkenyl, lower alkynyl, lower cycloalkyl, lower cycloalkyl lower alkyl, aryl, aryl lower alkyl, a heterocyclic group or a heterocyclyl lower alkyl, which may be optionally substituted by one or more lower alkoxy, lower alkylthio, halogen, lower alkyl, nitro, hydroxy, acyloxy, carboxy, carbalkoxy, lower alkylcarbonyl, lower alkylsulfonyl, lower alkoxysulfonyl, amino lower alkyl amino or acylamido groups, h) acetoxy;

i) a group —$OCOR_{11}$, wherein $R_{11}$ is
   ia) a straight or branched chain alkyl group of 2 to 7 carbon atoms, which may be interrupted by oxygen, sulfur or imino, and substituted by cyano, carboxyl, alkoxycarbonyl, hydroxy, carboxycarbonyl, halogen or amino;
   ib) a straight or branched chain alkenyl group of 2 to 7 carbon atoms, which may be interrupted by oxygen, sulfur or imino;
   ic) optionally substituted aryl, heterocyclyl or cycloalkyl; or
   id) arylalkyl, heterocyclyl-alkyl or cycloalkylalkyl, which may be substituted in the ring;

j) a group of formula

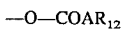

wherein

A is oxygen, sulfur or imino and $R_{12}$ is hydrogen, methyl or $R_{11}$;

k) a group of formula

wherein Q is fluorine, chlorine, bromine or iodine and E is an integer of 1 to 4, and $R_2$ represents hydrogen, a cation, a carboxy-protecting group or $COOR_2$ is $COO^{31}$, when $R_1$ is a positive charged group, comprising in step (ii) reacting the mixed carboxylic acid anhydride with a compound of formula II

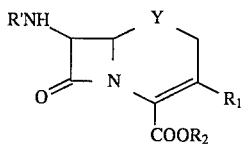

wherein Y, $R_1$ and $R_2$ are as defined above and R' is hydrogen or an amino protecting group.

3. A process according to claim 2 wherein step (ii) is effected by mixing a solution or suspension of a salt of a 7-amino-ceph-3-em -4-carboxylic acid in a $(C_{3-4})$alkanol, with the mixed carboxylic acid anhydride.

4. A process according to claim 1, 2 or 3 wherein the mixed carboxylic acid anhydride is produced in the presence of a pyridine.

5. A process according to claim 2 wherein the mixed carboxylic acid anhydride is of formula

wherein

R is phenyl, 4-hydroxyphenyl or 1,4-cyclohexadien-1-yl, $R_{13}$ is $(C_{1-3})$alkyl, $R_{14}$ is hydrogen or $(C_{1-3})$ alkyl group, $R_{15}$ is a $(C_{1-4})$ alkyl, $(C_{1-4})$ alkoxy, phenyl or phenyl substituted by alkoxy and, $R_{16}$ is an aliphatic, alicyclic or aromatic group.

6. A process according to claim 2 wherein the mixed carboxylic acid anhydride is produced from an acylating agent which is a reactive acid derivative of a $C_4$–$C_9$ alkanoic acid or benzoic acid.

7. A process according to claim 6 wherein the acylating agent is pivaloyl chloride, 2-ethylhexanoyl chloride or benzoyl chloride.

8. A process according to claim 2 wherein the mixed carboxylic acid anhydride is produced in a solvent which comprises an ester or a ketone.

9. A process according to claim 8 wherein the solvent is n-butyl acetate.

10. A process according to claim 8 wherein the solvent is methyl isobutyl ketone.

11. A process according to claim 8 wherein the solvent is isopropyl acetate.

12. A process according to claim 13 wherein the co-solvent is selected from formamide, acetamide, N,N-dimethyl formamide, N-methylacetamide, N,N-dimethylacetamide, N-methylpyrrolidine, tetramethylurea and isopropanol.

13. A process according to claim 2 which comprises using a cosolvent in steps (i) and (ii).

14. A process according to claim 2 for the preparation of a 7-alpha-aminoacyl-cephem derivative of the formula

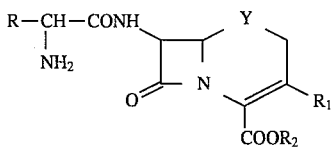

where
- R is phenyl, 4-hydroxyphenyl, or 1,4-cyclohexadien-1-yl,
- Y is oxygen, sulfur, or methylene,
- $R_1$ is hydrogen, halogen, $(C_{1-4})$alkoxy, —CH=$CHR_3$, or —$CH_2Z$, where
- $R_3$ is hydrogen, $(C_{1-6})$alkyl, or phenyl, and
- Z is —$SR_9$ or acetoxy, where
- $R_9$ is 1-methyl-1H-tetrazol-5-yl or 1,2,3-triazol-5-yl and
- $R_2$ is hydrogen, comprising the steps of:
  i) preparing a mixed carboxylic acid anhydride of formula III

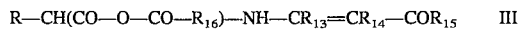

wherein
- R is as defined above,
- $R_{13}$ is $(C_{1-3})$ alkyl,
- $R_{14}$ is hydrogen or $(C_{1-3})$ alkyl,
- $R_{15}$ is $(C_{1-4})$ alkyl, $(C_{1-4})$ alkoxy, or phenyl, and
- $R_{16}$ is $(C_{3-8})$ alkyl or phenyl, by reacting a sodium, potassium, dicyclohexylammonium, N-methylpiperidinium, or N-methylmorpholinium salt of

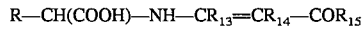

with a reactive acylating derivative of an acid of the formula

where R, $R_{13}$, $R_{14}$, $R_{15}$, and $R_{16}$ are as defined above, and
  ii) reacting the mixed carboxylic acid anhydride of formula III with a compound of formula II

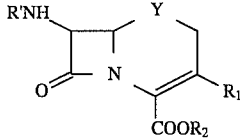

where R' is hydrogen and Y, $R_1$, and $R_2$ are as defined above; and
  iii) deprotecting the product;

wherein
- step i) is carried out in a non-halogenated solvent selected from methyl-$(C_{2-4})$alkyl ketone, di-$(C_{2-4})$alkyl ketone, $(C_{1-3})$alkanoic acid butyl ester, $(C_{1-3})$alkanoic acid propyl ester, and toluene, and carrying out
- step ii) with an unprotected compound of formula II in a non-halogenated solvent selected from $(C_{1-4})$alkanol and a combination of $(C_{1-4})$alkanol and a solvent of step i) and
- step iii) deprotecting the product by splitting off the N-substituted vinyl group by hydrolysis in aqueous acid to obtain the compound of formula I.

15. A process according to claim 14 in which the salt used in step i) is a Dane salt selected from sodium and potassium
1) D-N(1-methoxycarbonylpropen-2-yl)-α-aminophenylacetate;
2) D-N(1-ethoxycarbonylpropen-2-yl)-α-aminophenylacetate;
3) D-N(1-methoxycarbonylpropen-2-yl)-α-amino-p-hydroxyphenylacetate;
4) D-N(1-ethoxycarbonylpropen-2-yl)-α-amino-p-hydroxyphenyl acetate; and
5) D-N(1-methoxycarbonylpropen-2-yl)-α-amino-2-(1,4-cyclohexadien-1-yl)acetate.

16. A process according to claim 14 in which the 7-aminoceph-3-em-4-carboxylic acid is selected from
a) 7-aminocephalosporanic acid;
b) 3-chloro-7-amino-3-cephem-4-carboxylic acid;
c) 3-[(1-methyl-1H-tetrazol-5-yl)thiomethyl]-7-amino-3-cephem-4-carboxylic acid;
d) 3-methoxy-7-amino-3-cephem-4-carboxylic acid; and
e) 3-propenyl-7-amino-3-cephem-4-carboxylic acid.

17. A process according to claim 14 in which the reactive acylating derivative of an acid is pivaloyl chloride, 2-ethylhexanoyl chloride, or benzoyl chloride.

* * * * *